United States Patent
Wist et al.

(10) Patent No.: US 7,587,235 B2
(45) Date of Patent: Sep. 8, 2009

(54) METHOD FOR ASSIGNING DIGITAL IMAGE INFORMATION TO THE NAVIGATIONAL DATA OF A MEDICAL NAVIGATION SYSTEM

(75) Inventors: Henrik Wist, München (AT); Alf Ritter, Erdweg (DE); Mario Zeiss, Poing (DE); Hanna Rotermund-Buwen, Zirndorf (DE); Helmar Werner Lang, Zirndorf (DE); Jörg Peter Strobel, Forchheim (DE); Klaus-Peter Kreuzer, Furth (DE)

(73) Assignee: BrainLAB AG, Feldkirchen (DE)

( * ) Notice: Subject to any disclaimer, the term of this patent is extended or adjusted under 35 U.S.C. 154(b) by 1484 days.

(21) Appl. No.: 10/150,877

(22) Filed: May 16, 2002

(65) Prior Publication Data

US 2003/0139670 A1    Jul. 24, 2003

(30) Foreign Application Priority Data

Jan. 18, 2002    (EP)    .................................. 02001038

(51) Int. Cl.
*A61B 5/05*    (2006.01)
(52) U.S. Cl. ...................................... 600/425; 606/130
(58) Field of Classification Search ................. 600/414, 600/417, 426, 429, 407, 424; 606/130
See application file for complete search history.

(56) References Cited

U.S. PATENT DOCUMENTS

| | | | | |
|---|---|---|---|---|
| 4,159,462 A | * | 6/1979 | Rocha et al. ................... | 367/97 |
| 4,733,562 A | * | 3/1988 | Saugeon ....................... | 73/626 |
| 6,072,177 A | * | 6/2000 | McCroskey et al. ....... | 250/252.1 |
| 6,115,626 A | * | 9/2000 | Whayne et al. ............. | 600/427 |
| 6,298,259 B1 | * | 10/2001 | Kucharczyk et al. ........ | 600/411 |
| 6,501,981 B1 | * | 12/2002 | Schweikard et al. ........ | 600/427 |
| 6,895,268 B1 | * | 5/2005 | Rahn et al. ................... | 600/429 |
| 2001/0031919 A1 | * | 10/2001 | Strommer et al. ........... | 600/424 |
| 2001/0036245 A1 | | 11/2001 | Kienzle, III | |

FOREIGN PATENT DOCUMENTS

WO    PCT/US00/07374    3/2000

* cited by examiner

*Primary Examiner*—Brian Casler
*Assistant Examiner*—Parikha S Mehta
(74) *Attorney, Agent, or Firm*—Renner, Otto, Boisselle & Sklar, LLP

(57) ABSTRACT

A method for assigning digital image information to the navigational data of a medical navigation system is provided. The method includes:
producing digital image information from a digital image recording device for a patient being monitored by means of the navigation system;
transmitting a signal from the image recording device to the navigation system when an image is produced, the signal including assignment information for assigning the image information to the navigational data which apply to the image information; and
transmitting the image information from the image recording device to the navigation system, wherein
the image information and the corresponding navigational data are assigned to each other.

17 Claims, 2 Drawing Sheets

Figure 1:
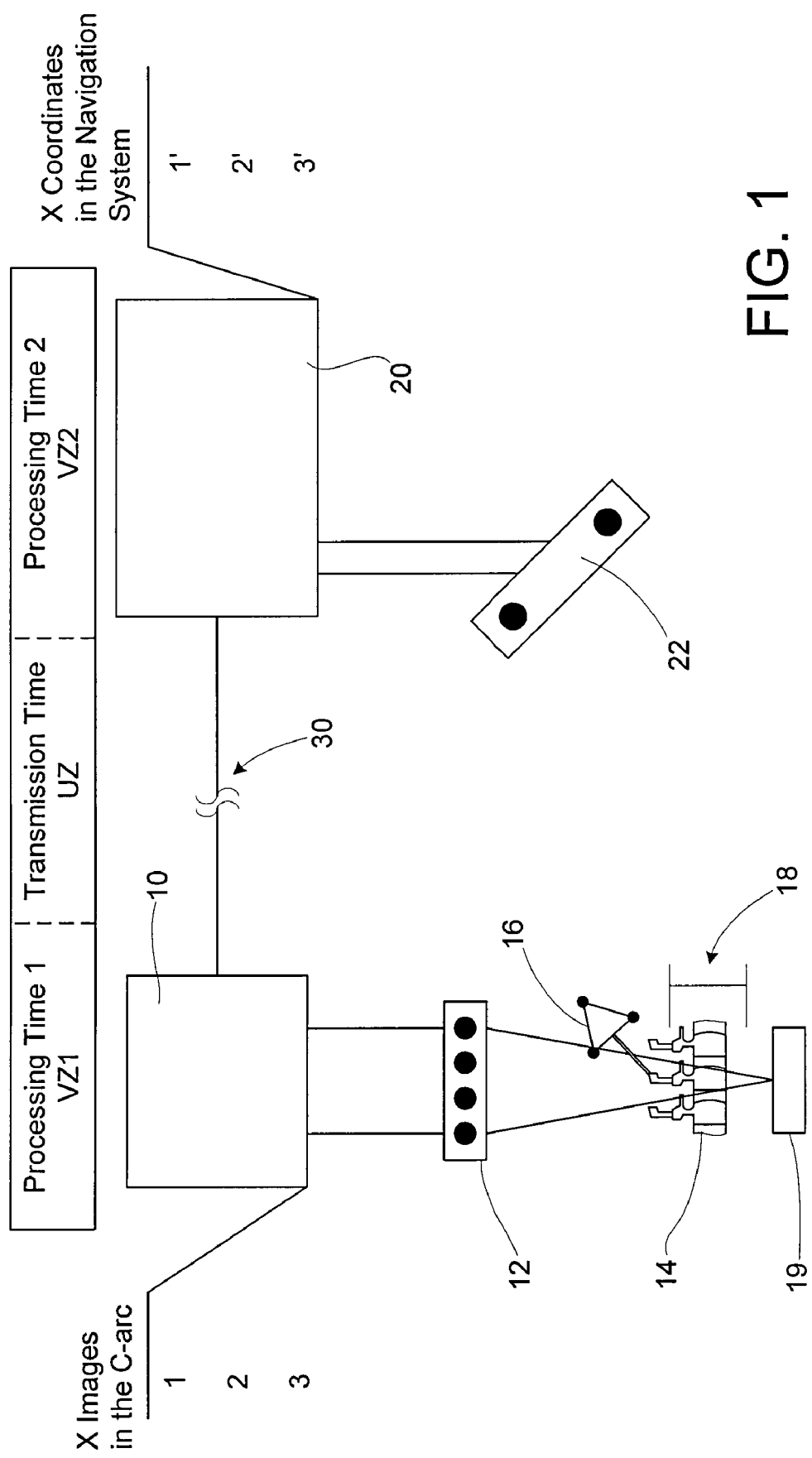

METHOD FOR ASSIGNING DIGITAL IMAGE INFORMATION TO THE NAVIGATIONAL DATA OF A MEDICAL NAVIGATION SYSTEM

The present invention relates to assigning digital image information to the navigational data of a medical navigation system. In particular, the invention is to be used in the area of apparatus support in, among other things, orthopaedic surgery, and so-called image-assisted surgery ('image guided surgery').

Specifically in surgery on a patient's spine, it is particularly important to operate with great accuracy, and to assist the physician in this respect, medical navigation systems are increasingly often used, which allow the patient and instruments to be tracked and offer a visual aid in performing operations. Such a medical navigation system is known for example from DE 196 39 615 C2. In order to be able to provide visual support which is as optimal as possible, the images from the navigation system, deriving from tomographic imaging (CT, MR, PET) produced beforehand, can be supplemented by additionally including, among other things, x-ray images or image information about the patient in the information which the physician is provided, since such x-ray images allow highly accurate representations of the bone structures. The x-ray images are mostly produced using mobile C-arc x-ray devices, and the important thing here is to ensure that the x-ray image produced for the part of the patient's body is accurately assigned to the positional and image data for the same provided by the navigation system, in order that the information from the x-ray image is also displayed on the screen of the navigation device in the correct positional relationship. U.S. Pat. Nos. 5,799,055, 3,577,160, 5,788,431, 5,967,982 and 5,772,594 deal with such x-ray image registering within the framework of surgical navigation methods.

In all of these methods, an analogue technique is still used which works with the aid of an analogue video signal output at the C-arc, BNC cables and a video signal input at the computer system. In this way, the image information of the C-arc is continuously available at the video signal input of the navigation system, just as the tracking information of the medical navigation system is constantly and currently provided. The computer system of the navigation system then processes and "registers" the video data, i.e. the system determines the exact position of the image data in relation to a pre-defined reference, for example on the patient. It is then possible, on the basis of said obtained image data, to also display the position of an instrument in "real time" with respect to the displayed bone structure from the x-ray image, i.e. to provide a navigating aid for the physician.

In the analogue systems currently known, registration is started either manually or with the aid of complex x-ray sensors. The manual method does not take into account possible patient movement between imaging at the C-arc and imaging at the navigation system, and the sensory method incorporates a very high error rate due to the additional sensors.

Digitally operating C-arc x-ray devices are currently being introduced onto the market increasingly often, which can provide high-resolution images and also have the option of storing multiple images. It is also desirable to employ such digital C-arc x-ray devices, which provide digital image information, within the framework of navigating with the aid of registered x-ray images, however technical conversion problems still exist connected with the fact that after the digital x-ray image has been produced, a processing time arises in the C-arc, and a certain period of time is also required as a whole to transmit signals from the C-arc to the navigation system. Thus, a certain period of time can pass before the navigation system obtains a processed image and is then able to detect the corresponding patient position in the navigation system. In this time, however, the patient or the C-arc can have moved, even if this movement is caused merely by breathing. There is therefore in principle a danger of mis-registration.

It is the object of the present invention to solve the above problems and to enable image information to be registered in a navigation system, even for images from digital image recording devices, such as for example a digital C-arc x-ray device. In particular, the intention is to provide a method for assigning digital image information to the navigational data of a medical navigation system, wherein there is no danger of mis-registration due to time delays in transmitting the image information.

In one aspect of the present invention, this object is solved by a method for assigning digital image information to the navigational data of a medical navigation system, wherein: digital image information from a digital image recording device is produced for a patient being monitored by means of the navigation system; in producing said image, a signal is sent from the image recording device to the navigation system, which includes assignment information for assigning the image information to the navigational data which apply to said image information; said image information is sent from the image recording device to the navigation system; and said image information and the corresponding navigational data are assigned to one another.

The advantageous nature of the present invention is based in particular on transmitting a signal (telegram) from the image recording device to the navigation system while producing the image. Delivering this signals informs the navigation system that digital image information is being produced at a particular point in time, and since such a signal need not necessarily include the image information itself, it can be dispatched from the image recording device with any time delay. Thus, digitally delivering the data for navigation is only then enabled, and can be performed with at least the same accuracy as with the aid of the conventional method in which an analogue image is constantly available at the navigation system. The delay between recording and delivering the image data from the digital image recording device to the navigation system is bridged with the aid of this signal, such that a very high registering accuracy can be achieved, wherein the advantages of digital information come to fruition, namely high resolution and accuracy and the option of storing the information.

The nature of the signal sent from the image recording device to the navigation system can be variable within the framework of the present invention. The assignment information inherent in the signal can for example be information which merely informs the navigation system that image information has been produced. Thus, it is possible to just transmit a kind of "ping" signal from the digital image recording device to the navigation system when an image is produced, wherein receiving the "ping" signal automatically triggers the navigation system to assign the navigation data detected at said point in time to the image information which was produced when the ping signal was sent. It is thus possible, even if the actual image, i.e. the actual image information, only arrives at the navigation system sometime after being processed at the C-arc, to assign the correct navigational data to said image information and therefore to correctly register the image in the navigation system.

In an embodiment of the method in accordance with the invention, the assignment information includes one or more items of information about the image produced; this information can in particular include an image number, time of image production and other information about the properties of the image (for example, calibration information for said image information) or about the patient. Digital information is conventionally produced and stored in the form of header information plus a corresponding image. In the header information, identification features can also be assigned to the actual image, for example image number, time of image production, resolution, designation of the image recording device, etc. It is then for example possible in accordance with an embodiment variant of the invention to transmit just this header information and a blank image in the signal sent when an image is produced, since practically no time is required to produce this header information. The image can then follow later and be assigned in the navigation system to the identical header information and the navigational data produced for this header.

Furthermore, it is possible to also record reference information about the image in the signal (telegram), for example about the spatial position of the image, which is particularly advantageous when the image is rotated or shifted by software, for viewing. Data concerning the position of the image intensifier or display information (for example, contrast) can likewise be transmitted.

In rare cases in which it is possible to keep the processing time at the image recording device for the image information exceedingly short, it is also possible within the framework of the present invention to transmit the entire image together with the signal and the assignment information to the navigation system simultaneously. This is an optimal situation for the method in accordance with the present invention, which however also ensures the security that longer processing times do not lead to inaccuracies in registration.

In general, however, the digital image information does not have to be processed and stored until it is in the image recording device, wherein a certain period of time passes. In accordance with its preferred embodiment, the present invention therefore also detects those cases in which the image information is transmitted deferred with respect to transmitting the signal to the navigation system. Successively produced image information and/or the assigned navigational data are preferably retrievably stored, for example in the image recording device and the navigation system respectively, or in one of the two units, or in a separate, central memory. Thus, when image data are sent to and received by the navigation system later than the signal when an image is produced, the positional data which the navigation system stored upon receiving the signal are assigned to the image data which also carry the coding of the signal. By accurately recording the position of the image recording device and the patient, it is therefore possible to accurately register for navigation.

It would be possible in another variant to increase the accuracy further by the navigation system continuously storing the positional data of the image recording device and the patient. Upon receiving the signal and the assignment information, it can then calculate back to an earlier position coordinate. In other words, the time delay between the time of producing the image information and the time of capturing the navigational data is determined beforehand and is taken into account or calculated out when assigning the image information to the navigational data.

Such a system is particularly helpful when sending the signal with the assigning information also takes an appreciable period of time. Often, digital image recording devices and navigation systems are not directly connected to each other but via a data intranet, which necessarily can lead to relevant delays in transmitting the signal. In such a case, it is particularly advantageous if, in accordance with a variant of the method in accordance with the invention, the time delay between the time of transmitting the signal and the time of capturing the navigational data is determined beforehand and taken into account or calculated out when assigning the image information to the navigational data. This also applies in the case of wireless communication between the devices, for example in a wireless data transmission network, in which delays can arise for example due to transmission faults. The present invention is also particularly suitable for this.

In a preferred embodiment of the present invention, the digital image information includes an x-ray image produced by a C-arc x-ray device which digitally captures and processes the x-ray image data.

The present invention further comprises a program which, when it is running on a computer or is loaded on a computer, causes the computer to perform the method as explained above in its embodiment variants. The invention further comprises a computer program storage medium comprising such a program.

In accordance with another aspect of the present invention, the latter relates to a means for assigning digital image information to the navigational data of a medical navigation system, comprising: a digital image recording device which produces digital image information for a patient being monitored by means of the navigation system; a signal transmission means by means of which a signal is transmitted from the image recording device to the navigation system when an image is produced, said navigation system including assignment information for assigning the image information to the navigational data which apply to said image information; an image transmission means by means of which the image information is transmitted from the image recording device to the navigation system; and a data processing means by means of which the image information and the corresponding navigation data are assigned to each other.

Figure 2:
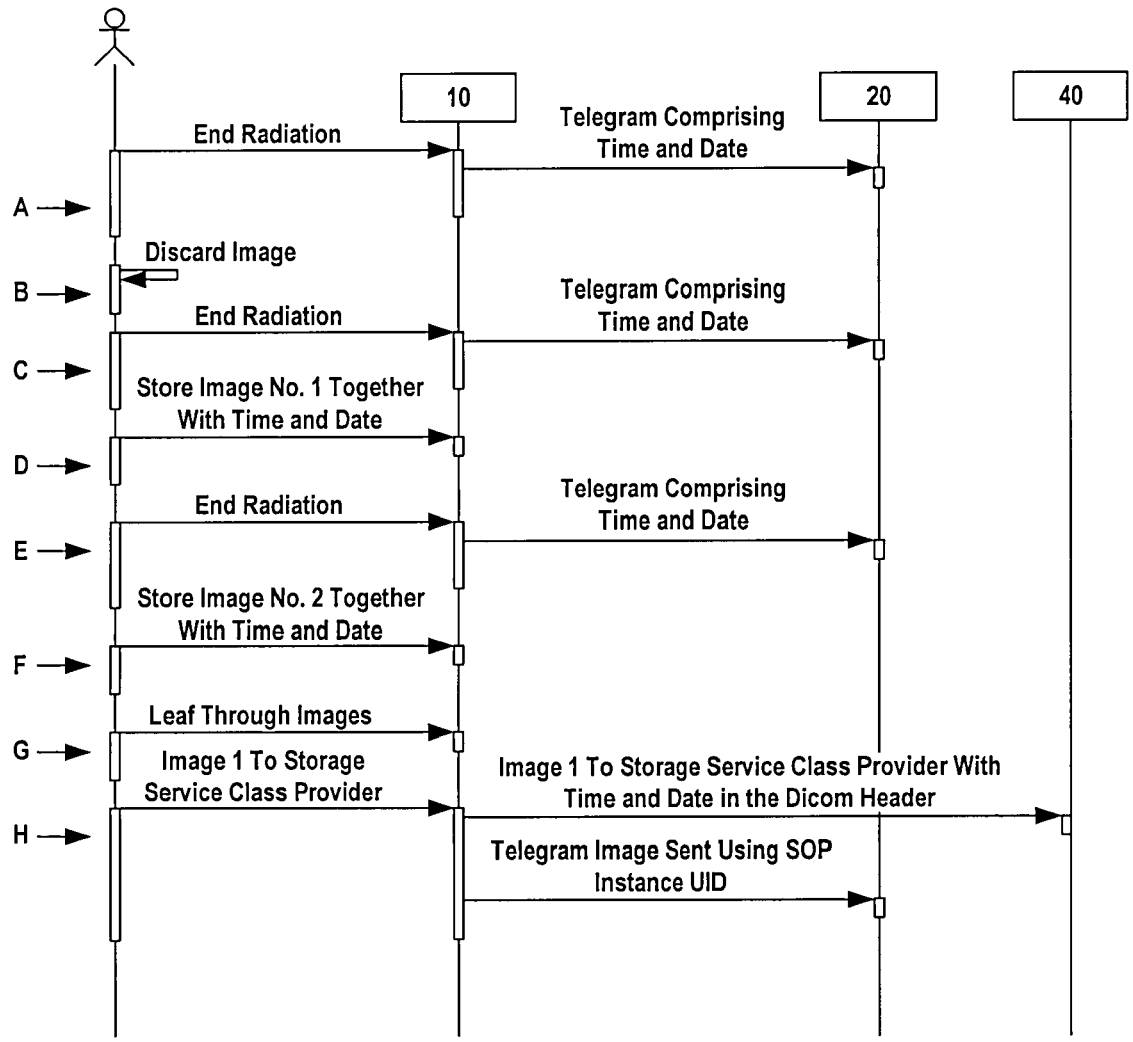

The invention will now be explained in more detail with the aid of the enclosed drawings and by way of example embodiments. FIG. 1 is a sketch of the apparatus arrangement and signal transfer in a system in accordance with the invention, while FIG. 2 shows a flow or interaction diagram for the sequence of a method in accordance with the invention.

The most important hardware components are systematically shown in FIG. 1 being the C-arc 10, to which a reference means 12 is attached, with which among other things its position in the navigation system can be determined. By means of the C-arc 10, x-ray images of a patient 14 are produced, who can also be tracked, i.e. positionally tracked and determined, by the navigation system by means of the reference means 16. Reference numeral 18 indicated that the patient may move.

The image of the C-arc is recorded on an image recorder 10, where reference numeral 19 indicates the x-ray source.

The C-arc 10 is a digitally operating C-arc which can process the information arriving at the image recorder 10 into digital images and store them. As shown on the left of the C-arc 10, three images have for example been produced using the present system, said images being numbered sequentially with the FIGS. 1, 2, 3. In practice, the system operator will produce individual images until he finds one which shows the important physical features in just such a way as is optimal for superimposing the x-ray image onto the image material assisting the operation. In this way, the image information arriving at the image recorder 19 is continuously processed into digital images, and these can also be directly stored in a memory of the C-arc, such that they can be retrieved later.

In order to later be able to correctly superimpose the x-ray images onto the image material of the navigation system during the operation, the position of the patient at the time the x-ray image was taken has to be known, and therefore the position of the patient 14 is detected via the reference means 16 when the x-ray image is being produced, by means of the navigation system 20 which detects the reference means 16 in relation to a reference or reference means 12 on the C-arc, via a camera system 22. In principle, the possibility would then exist of providing the operator with a switch which when activated informs the navigation system that an x-ray image is being produced at that moment, although such an approach is susceptible to errors if for example the trigger is activated too late, and the attempt should moreover be made to keep the operating effort as low as possible.

The present invention then intervenes here, by optimizing the data connection and signal transfer between the C-arc 10 and the navigation system 20. Such a connection is shown as an interface circuit 30 between the C-arc 10 and the navigation system 20. Via this circuit 30, information can be transmitted from the C-arc to the navigation system, and this connection 30 can on the one hand be a cable connecting the two devices directly to each other; it is possible on the other hand to connect the two devices via an intranet.

The essential problem is then a time delay between recording the x-ray image and the navigation system determining the position, which can have two causes. The first cause is the processing time VZ1 at the C-arc. For because it has to be processed digitally, the x-ray image is often not available at the immediate time of image production, but rather only later. If, in such a case, this x-ray image is transmitted to the navigation system via the interface circuit 30, in order to trigger navigational detection, i.e. determining the position of the patient 14, it is quite possible that the patient has already moved somewhat in the elapsed time, wherein such movement can result merely from breathing. The navigation system 20 would then assign navigational data to the obtained image which no longer correspond positionally to those which were valid for the time of image production. For this reason, a signal is transmitted in accordance with the present invention from the C-arc 10 to the navigation system 20 when an image is produced, which includes assignment information for assigning the image information, wherein such a signal can be transmitted immediately as the image is produced since it need not necessarily include the image itself.

In the example shown, the signal is one which comprises the number of the image, i.e. 1, 2 or 3, as the assignment information. This signal can be generated in the C-arc practically without a time delay, and transmitted via the interface circuit 30 to the navigation system 20. The navigation system can then detect the position and assign the co-ordinates 1', i.e. the corresponding navigational data, to the x-ray image 1, practically at the time of image production (for example in the case in which the C-arc 10 and the navigation system 20 are directly connected to each other by cable). When the image 1 is then transmitted from the C-arc 10 to the navigation system 20 via the interface circuit 30 at a later time, this is not damaging since the navigational data 1' already captured beforehand are already available there, even if the patient 14 has moved in the meanwhile. This process can of course be used be carried out for all the images 1, 2, 3 produced, to which chronologically correct navigational data or co-ordinates 1', 2', 3' are then assigned.

The assignment information need not always be an image number. It can also consist merely of a short trigger signal, a so-called ping, or can also include a number of items of information to be generated quickly, such as for example time, date, calibration information, patient information and the like. If numbering is used, this can be reset to zero every time the two systems are re-started. In order to ensure even greater security when assigning, it is also possible within the framework of an advantageous embodiment of the invention to synchronize the timing, i.e. the clocks in the C-arc and the navigation system. In any case of doubt, it is then possible while assigning to fall back on the absolute time transmitted within the context of the telegram (signal).

Among other things, the present invention therefore covers the case in which the image processing time at the C-arc leads to delays in navigational detection. If, however, it has been established for certain beforehand that the image processing does not require any relevant period of time, the image itself can also be transmitted together with the signal and the assignment information. The invention also comprises such cases, but offers counter-insurance for C-arcs having relatively slow image processing.

Another problem which is solved by a specific embodiment of the present invention arises due to the possibly relevant transmission time ÜZ between the C-arc 10 and the navigation system 20 (for example, if the two are connected to each other via a data intranet) and by the processing time VZ2 at the navigation system. At worst, the two time delays ÜZ and VZ2 as a whole also cause a delay in the navigation system recording the co-ordinates with respect to the time of image production, however this problem can also be solved in accordance with the invention. For the transmission time ÜZ and the processing time VZ2 can be established beforehand. If the navigation system then continuously stores the positional data of the C-arc and the patient, then once the signal has been processed in the navigation system, the fact can be calculated in that the time of image production must have been earlier, by the time difference ÜZ+VZ2, and the stored navigational data valid for this earlier time are then used to assign the image information. The delay from transmission time ÜZ and the processing time VZ2 at the navigation system are thus "calculated out", and because the processing time VZ1 has already been "mitigated" beforehand by transmitting the signal before the image in accordance with the invention, optimum accuracy in assigning the navigational data and the x-ray image may be achieved in accordance with this advantageous embodiment, even when a very slow intranet forms the connection between the navigation system and the C-arc and the navigation system exhibits an appreciable processing time of its own.

FIG. 2 shows a flow or interaction diagram for the sequence of a method in accordance with the invention. As shown at the top of FIG. 2, there is an interaction between a symbolically indicated operator, the C-arc 10, the navigation system 20 and a server (for example, a so-called Dicom server) indicated by the reference numeral 40, being an image memory or image archive. The server 40 can be an image memory of the hospital network and/or another external image memory, though in principle the image memory of the navigation system 20 can also be used.

The operator initiates each of the processes described in the following, which are indicated in FIG. 2 by the steps A to H. In the first step A, the operator generates an image at the C-arc 10, i.e. he initiates radiation and ends it. At this point, the C-arc 10 sends a telegram to the navigation system 20, i.e. a signal such as indicated in the previous description. As likewise described already, this telegram does not comprise the generated image itself, which still has to be digitally processed in the C-arc 10, but in the present example embodiment comprises only time and date information. This information can be immediately produced and forwarded, such that this does not cause a time delay. The navigation system 20 then stores the position of the C-arc 10 via a reference means 12 arranged on it, as well as the position of the patient via the reference means which is indicated in FIG. 1 by the reference numeral 16, together with the specific telegram information.

In step B, the operator establishes by viewing the image that it is unsuitable because it does not provide information on the important body parts, for example due to poor contrast. He discards the image, and in step C produces a new image, wherein the same processes then are run as for step A, namely initiating radiation, ending radiation and transmitting a telegram.

In step D, the operator establishes that the image fulfils the quality criteria and stores it in the C-arc image memory as image No.1, together with the corresponding time and date.

In step E, another image is then recorded and a telegram transmitted as in steps A to D, and in step F the operator establishes that the image produced in step E is also of good quality, and it is likewise stored in the C-arc image memory.

In this way, a multitude of images may be produced, and in step G the operator can leaf through the images produced, on a display device (monitor) and isolate the one which in his opinion provides the best representation. In the present case, this is image No.1, and in step H the operator gives the instruction to register image No.1 in the navigation system on the one hand, and on the other to send it to the image memory 40. To this end, image No. 1 is read from the memory at the C-arc, and the whole information, i.e. the image itself together with the telegram data (time, date), is forwarded. The navigation system 20 then obtains this comprehensive data set on the one hand, and by adjusting the telegram information, the image can then be assigned to the positional data recorded by the navigation system in step C, specifically to the relative position between the patient and the C-arc 10 present when image No.1 was produced. The image, together with the telegram information, is on the other hand also stored again in a separate memory 40 to be used again.

It becomes clear from this example embodiment that the method in accordance with the invention not only enables inaccuracies due to undesired delays (processing times, transmission times) to be avoided, but also allows desired delays, such as for example arise when an operator records a number of images and wishes to isolate the optimal one.

The invention claimed is:

1. A method for assigning digital image information to the navigational data of a medical navigation system, comprising:
   producing digital image information from a digital image recording device for a patient being monitored by said navigation system;
   transmitting a signal from said image recording device to said navigation system when an image is produced, said signal including assignment information for assigning said image information to navigational data which apply to said image information
   transmitting said image information from said image recording device to said navigation system; and
   assigning said image information and said corresponding navigational data to each other based on the signal such that the assigned image information and captured navigational data relate to substantially the same instant in time.

2. The method as set forth in claim 1, wherein said assignment information includes information which informs said navigation system that image information has been produced.

3. The method as set forth in claim 1, wherein said assignment information includes one or more items of information about said image information.

4. The method as set forth in claim 3, wherein said assignment information includes one or more of the following items of information:
   an image number;
   a time of image production; or
   information on properties of said image.

5. The method as set forth in claim 1, wherein said image information is transmitted as the same time as said signal is transmitted to said navigation system.

6. The method as set forth in claim 1, wherein said transmission of to the image information is delayed with respect to said transmission of the signal to said navigation system.

7. The method as set forth in claim 1, wherein successively produced image information and/or said assigned navigational data are retrievably stored.

8. The method as set forth in claim 6, wherein the time delay between the time of producing said image information and the time of capturing said navigational data for an existing data transmission system is determined prior to producing the digital image information, and the time delay is calculated when assigning said image information to said navigational data.

9. The method as set forth in claim 6, wherein the time delay between the time of transmitting said signal and the time of capturing said navigational data for an existing data transmission system is determined prior to producing the digital image information, and the time delay is calculated when assigning said image information to said navigational data.

10. The method as set forth in claim 1, wherein said digital image information includes an x-ray image or x-ray images produced by a C-arc x-ray device which digitally captures and processes said x-ray image data.

11. A program embodied on a computer readable medium for assigning digital image information to navigational data of a medical navigation system, comprising:
    code that produces digital image information from a digital image recording device for a patient being monitored by said navigation system;
    code that transmit a signal from said image recording deice to said navigation system when an image is produced, said signal including assignment information for assigning said image information to navigational data which apply to said image information;
    code that transmits said image information from said image recording device to said navigation system; and
    code that assigns said image information and said corresponding navigational data to each other based on the signal such that the assigned image information and captured navigational data relate to substantially the same instant in time.

12. An apparatus for assigning digital image information to the navigational data of a medical navigation system, comprising:
    a digital image recording device that produces digital image information for a patient being monitored by said navigation system;
    a signal transmission device that transmits a signal from said image recording device said to navigation system when an image is produced, said signal including assignment information for assigning said image information to navigational data which apply to said image information;

an image transmission device that transmits said image information from said image recording device to said navigation system; and a data processing device that assigns said image information and said corresponding navigation data to each other based on the signal such that assigned image information and captured navigational data relate to substantially the same instant in time.

13. The apparatus of claim 12, wherein said assignment information includes information which informs said navigation system that image information has been produced.

14. The apparatus of claim 12, wherein said assignment information includes one or more items of information about said image information.

15. The apparatus of claim 14, wherein said assignment information includes one or more of the following items of information:

an image number;

a time of image production; or information on properties of said image.

16. The apparatus of claim 12, wherein successively produced image information and/or said assigned navigational data are retrievably stored.

17. The apparatus of claim 12, wherein said image recording device is a C-arc or x-ray device which digitally captures and processes x-ray image data, and said digital image information includes an x-ray image or x-ray images produced by said C-arc x-ray device.

* * * * *